United States Patent
Jing

(10) Patent No.: US 9,527,901 B2
(45) Date of Patent: Dec. 27, 2016

(54) RECOMBINANT BI-FUNCTIONAL FUSION PROTEINS, PREPARATIONS AND METHODS FOR TREATING DISEASE

(71) Applicant: Deqiang Jing, New York, NY (US)

(72) Inventor: Deqiang Jing, New York, NY (US)

(73) Assignee: MACROIMMUNE INC, New York, NY (US)

( * ) Notice: Subject to any disclaimer, the term of this patent is extended or adjusted under 35 U.S.C. 154(b) by 0 days.

(21) Appl. No.: 14/666,328

(22) Filed: Mar. 24, 2015

(65) Prior Publication Data

US 2015/0266942 A1 Sep. 24, 2015

Related U.S. Application Data

(60) Provisional application No. 61/969,276, filed on Mar. 24, 2014.

(51) Int. Cl.
| | |
|---|---|
| *C07K 14/71* | (2006.01) |
| *C07K 14/47* | (2006.01) |
| *C07K 16/10* | (2006.01) |
| *C07K 16/12* | (2006.01) |
| *A61K 39/00* | (2006.01) |

(52) U.S. Cl.
CPC ........... *C07K 14/71* (2013.01); *C07K 14/4703* (2013.01); *C07K 16/1063* (2013.01); *C07K 16/1253* (2013.01); *A61K 39/00* (2013.01); *C07K 2317/10* (2013.01); *C07K 2317/21* (2013.01); *C07K 2317/30* (2013.01); *C07K 2317/34* (2013.01); *C07K 2317/55* (2013.01); *C07K 2317/76* (2013.01); *C07K 2319/00* (2013.01); *C07K 2319/30* (2013.01)

(58) Field of Classification Search
CPC . C07K 14/71; C07K 14/4703; C07K 16/1063; C07K 16/1253; C07K 2317/10; C07K 2317/21; C07K 2317/30; C07K 2317/34; C07K 2317/55; C07K 2317/76; C07K 2319/00; C07K 2319/30; A61K 39/00
See application file for complete search history.

(56) References Cited

PUBLICATIONS

Mori F, et al. Blood Cancer Journal. 2:e67. 2012. Available online at -doi:10.1038/bcj.2012.12.*
Wang ES, et al. Proc. Am. Soc. Clin. Oncol. 22:210 (abstr 841). 2003. Available online at—http://www.iritis.org/phpBB3/viewtopic.php?t=1250.*
Chen HX, et al. Avaiulable online at—http://www.cancernetwork.com/review-article/current-clinical-trials-anti-vegf-monoclonal-antibody-bevacizumab#sthash.B4IeBN3C.dpuf. Aug. 1, 2001.*
Hayashi A, e al. J. Biol. Chem. 279(28):29450-29460. 2004. Available online at—DOI 10.1074/jbc.M400950200.*

Chao MP, Weissman IL, and Majeti R.The CD47-SIRPα Pathway in Cancer Immune Evasion and Potential Therapeutic Implications. Curr Opin Immunol. 2012, 24: 225-232.
Chao MP, Tang C, Pachynski RK, Chin R, Majeti R, Weissman IL. Extranodal dissemination of non-hodgkin lymphoma requires cd47 and is inhibited by anti-cd47 antibody therapy. Blood. 2011, 118:4890-4901.
Chao MP, Alizadeh AA, Tang C, Myklebust JH, Varghese B, Gill S, Jan M, Cha AC, Chan CK, Tan BT, Park CY, et al. Anti-cd47 antibody synergizes with rituximab to promote phagocytosis and eradicate non-hodgkin lymphoma. Cell. 2010, 142:699-713.
Majeti R, Chao MP, Alizadeh AA, Pang WW, Jaiswal S, Gibbs KD, Jr, Van Rooijen N, Weissman IL. CD47 is an adverse prognostic factor and therapeutic antibody target on human acute myeloid leukemia stem cells. Cell. 2009, 138:286-299.
Chao MP, Alizadeh AA, Tang C, Jan M, Weissman-Tsukamoto R, Zhao F, Park CY, Weissman IL, Majeti R. Therapeutic antibody targeting of cd47 eliminates human acute lymphoblastic leukemia. Cancer Res. 2011, 71:1374-1384.
Collins S.J. The HL60 promyelocytic leukemia cell line: proliferation, differentiation, and cellular oncogene expression. Blood. 1987, 70:1233-1244.
Xu Y and Scheinberg DA. Elimination of human leukemia by monoclonal antibodies in an athymic nude mouse leukemia model. Clin Cancer Res. 1995, 1:1179-1187.
Lin JJ, Hsu HY, et al. Molecular evidence of anti-leukemia activity of gypenosides on human myeloid leukemia HL-60 cells in vitro and in vivo using a HL-60 cells murine xenograft model. Phytomedicine. 2011, 18:1075-1085.
Sun Y, Xu HJ., et al. Crocin Exhibits Antitumor Effects on Human Leukemia HL-60 Cells In Vitro and In Vivo. Evidence-Based Complementary and Alternative Medicine. 2013, 2013:1-7.
Thomas LH, Friedland JS, Sharland M, Becker S. Respiratory Syncytial Virus-Induced RANTES Production from Human Bronchial Epithelial Cells Is Dependent on Nuclear Factor-κb Nuclear Binding and Is Inhibited by Adenovirus-Mediated Expression of Inhibitor of κBα. Journal of Immunology. 1998, 161: 1007-16.
Lin Y, Zhang M, Barnes PF. Chemokine production by a human alveolar epithelial cell line in response to *Mycobacterium tuberculosis*. Infection and Immunity. 1998, 66: 1121-6.
Xu X and Prestwich GD. Inhibition of Tumor Growth and Angiogenesis by a Lysophosphatidic Acid Antagonist in a Engineered Three-dimensional Lung Cancer Xenograft Model. Cancer. 2010, 116: 1739-1750.

(Continued)

*Primary Examiner* — Robert Landsman
(74) *Attorney, Agent, or Firm* — Kening Li; Miller Canfield

(57) ABSTRACT

A recombinant bi-functional fusion protein, comprising an Ig region of an extracellular domain of a signal-regulator protein (SIRP), linked via a Fc fragment of an Ig, to an Ig region of an extracellular domain of VEGFR, wherein the protein can bind to CD47 and VEGF simultaneously, blocking the binding of CD47 with the SIRP on the cell surface of macrophages to stimulate the phagocytosis of tumor cells by macrophages, and inhibiting the growth of vascular endothelial cells induced by VEGF. The present application also provides a nucleic acid molecule encoding the recombinant bi-functional fusion protein and an expression vector expressing the protein, a method for producing the protein and a method for treating a disease over-expressing CD47 or VEGF.

28 Claims, 6 Drawing Sheets

(56) References Cited

PUBLICATIONS

Coxon A, Ziegler B, et al. Antitumor activity of motesanib alone and in combination with cisplatin or docetaxel in multiple human non-small-cell lung cancer xenograft models. Mol Cancer. 2012, 11: 70.

Naumov GN, Nilsson MB, et al. Combined Vascular Endothelial Growth Factor Receptor and Epidermal Growth Factor Receptor (EGFR) Blockade Inhibits Tumor Growth in Xenograft Models of EGFR Inhibitor Resistance. Clin Cancer Res. 2009, 15: 3484-3494.

Magda D, Lecane P, et al. mtDNA depletion confers specific gene expression profiles in human cells grown in culture and in xenograft. BMC Genomics. 2008, 9: 521.

* cited by examiner

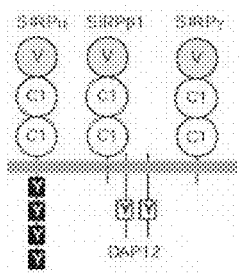
Figure 1: structure of SIRPs
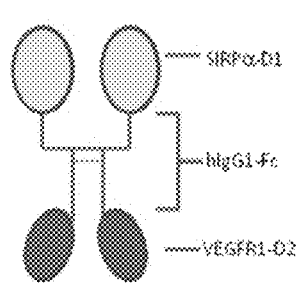 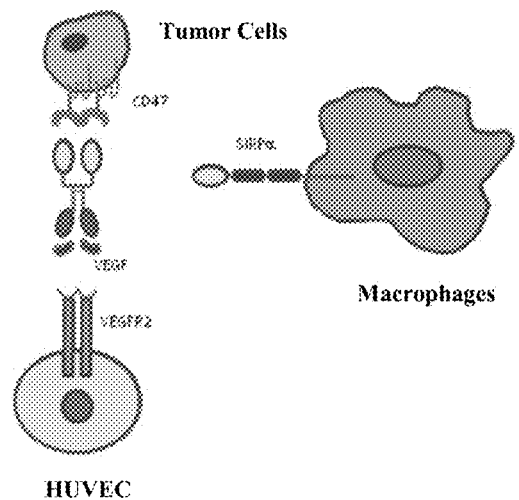
Figure 2: structure and mechanism of action of SIRPαD1-Fc-VEGFR1D2

A. Nucleic Acid Sequence

```
ATGGAGCCCG CCGGCCCGGC CCCGGCCGGC CTCGGCCCGC TGCTCTGCCT GCTGCTGGCC  60
GCGTCCTGCG CCTGGTCAGG AGTGGCGGGT GAGGAGGAGC TGCAGGTGAT TCAGCCTGAC 120
AAGTCCGTAT CAGTTGCAGC TGGAGAGTCG GCCATTCTGC ACTGCACTGT GACCTCCCTG 180
ATCCCTGTGG GGCCCATCCA GTGGTTCAGA GGAGCTGGAC CAGCCCGGGA ATTAATCTAC 240
AATCAAAAAG AAGGCCACTT CCCCCGGGTA ACAACTGTTT CAGAGTCCAC AAAGAGAGAA 300
AACATGGACT TTTCCATCAG CATCAGTAAC ATCACCCCAG CAGATGCCGG CACCTACTAC 360
TGTGTGAAGT TCCGGAAAGG GAGCCCTGAC ACGGAGTTTA AGTCTGGAGC AGGCACTGAG 420
CTGTCTGTGC GTGCCAAACC CTCTGCCCCC GTGGTATCGG GCCCTGCGG GAGGGCCACA 480
CCTCAGCACG AATTCGAGCC CAAATCTTGT GACAAAACTC ACACATGCCC ACCGTGCCCA 540
GCACCTGAAC TCCTGGGGGG ACCGTCAGTC TTCCTCTTCC CCCCAAAACC CAAGGACACC 600
CTCATGATCT CCCGGACCCC TGAGGTCACA TGCGTGGTGG TGGACGTGAG CCACGAAGAC 660
CCTGAGGTCA AGTTCAACTG GTACGTGGAC GGCGTGGAGG TGCATAATGC CAAGACAAAG 720
CCGCGGGAGG AGCAGTACAA CAGCACGTAC CGTGTGGTCA GCGTCCTCAC CGTCCTGCAC 780
CAGGACTGGC TGAATGGCAA GGAGTACAAG TGCAAGGTCT CCAACAAAGC CCTCCCAGCC 840
CCCATCGAGA AAACCATCTC CAAAGCCAAA GGGCAGCCCC GAGAACCACA GGTGTACACC 900
CTGCCCCCAT CCCGGGATGA GCTGACCAAG AACCAGGTCA GCCTGACCTG CCTGGTCAAA 960
GGCTTCTATC CCAGCGACAT CGCCGTGGAG TGGGAGAGCA ATGGGCAGCC GGAGAACAAC 1020
TACAAGACCA CGCCTCCCGT GCTGGACTCC GACGGCTCCT TCTTCCTCTA CAGCAAGCTC 1080
ACCGTGGACA AGAGCAGGTG GCAGCAGGGG AACGTCTTCT CATGCTCCGT GATGCATGAG 1140
GCTCTGCACA ACCACTACAC GCAGAAGAGC CTCTCCCTGT CTCCGGGTAA ACTCGAGATT 1200
AGTGATACAG GTAGACCTTT CGTAGAGATG TACAGTGAAA TCCCCGAAAT TATACACATG 1260
ACTGAAGGAA GGGAGCTCGT CATTCCCTGC CGGGTTACGT CACCTAACAT CACTGTTACT 1320
TTAAAAAAGT TTCCACTTGA CACTTTGATC CCTGATGGAA AACGCATAAT CTGGGACAGT 1380
AGAAAGGGCT TCATCATATC AAATGCAACG TACAAAGAAA TAGGGCTTCT GACCTGTGAA 1440
GCAACAGTCA ATGGGCATTT GTATAAGACA AACTATCTCA CACATCGACA AACCAATACA 1500
ATCTAA
```

B. Amino Acid Sequence

```
MEPAGPAPGRLGPLLCLLLAASCAWSGVAGEEELQVIQPDKSVSVAAGESAILHCTVTSL  60
IPVGPIQWFRGAGPARELIYNQKEGHFPRVTTVSESTKRENMDFSISISNITPADAGTYY 120
CVKFRKGSPDTEFKSGAGTELSVRAKPSAPVVSGPAARATPQHEFEPKSCDKTHTCPPCP 180
APELLGGPSVFLFPPKPKDTLMISRTPEVTCVVVDVSHEDPEVKFNWYVDGVEVHNAKTK 240
PREEQYNSTYRVVSVLTVLHQDWLNGKEYKCKVSNKALPAPIEKTISKAKGQPREPQVYT 300
LPPSRDELTKNQVSLTCLVKGFYPSDIAVEWESNGQPENNYKTTPPVLDSDGSFFLYSKL 360
TVDKSRWQQGNVFSCSVMHEALHNHYTQKSLSLSPGKLEISDTGRPFVEMYSEIPEIIHM 420
TEGRELVIPCRVTSPNITVTLKKFPLDTLIPDGKRIIWDSRKGFIISNATYKEIGLLTCE 480
ATVNGHLYKTNYLTHRQTNTI 501
```

Figure 3: nucleic acid and amino acid sequence of SIRPαD1-Fc-VEGFR1D2

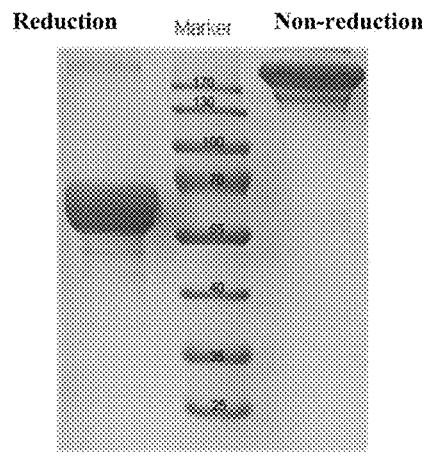
Figure 4: protein electrophoresis analysis of SIRPαD1-Fc-VEGFR1D2
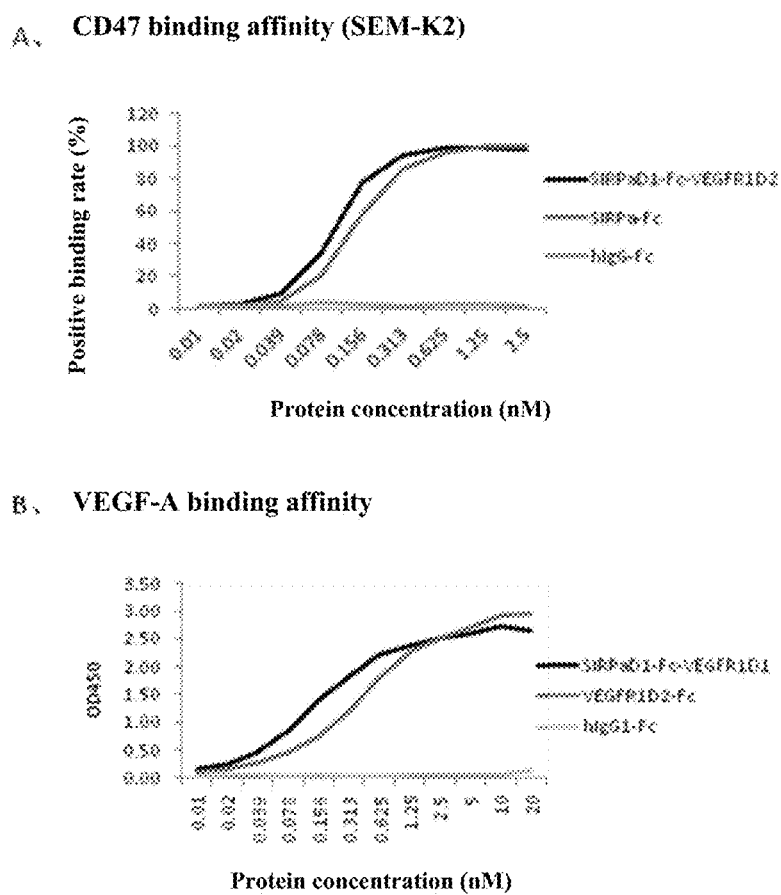
Figure 5: results of a target-binding affinity analysis

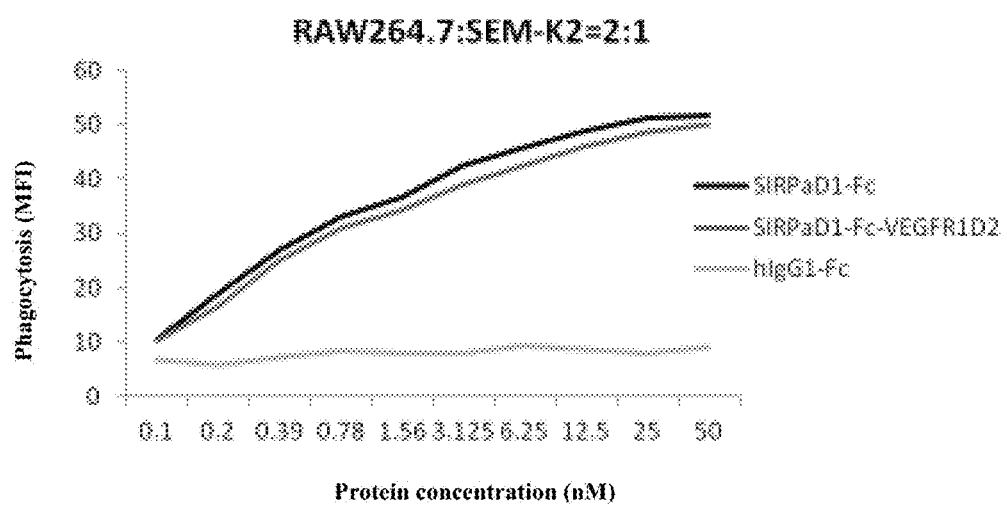
Figure 6: results of a target inhibiting assay

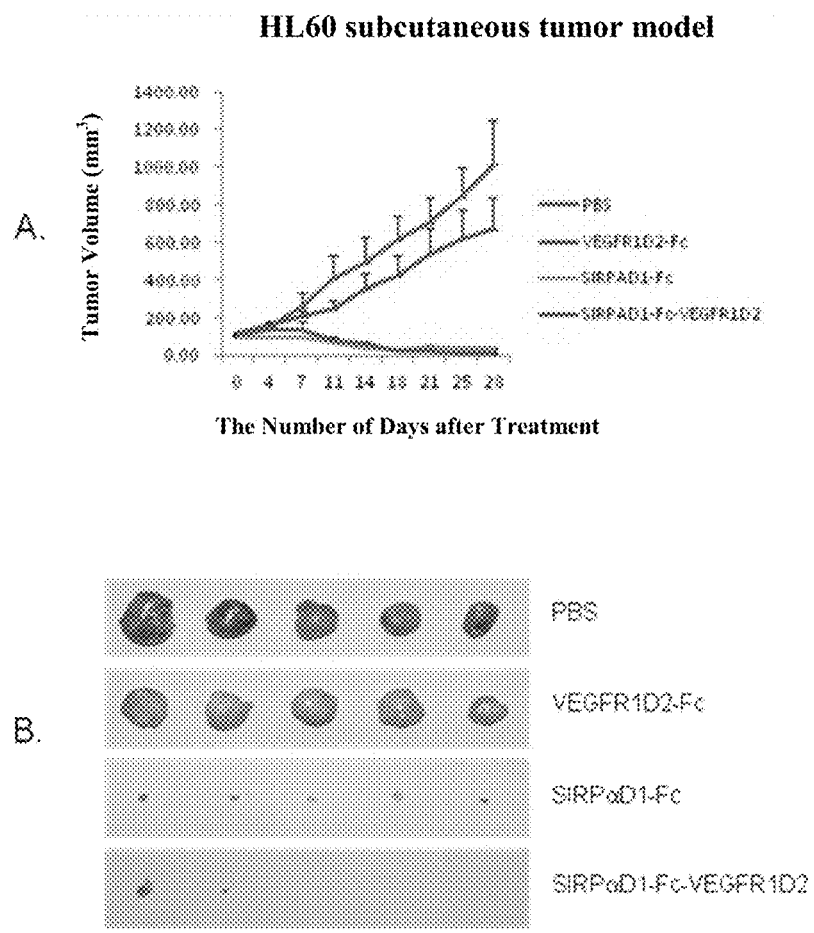
Figure 7: results of an *in vivo* anti-tumor assay

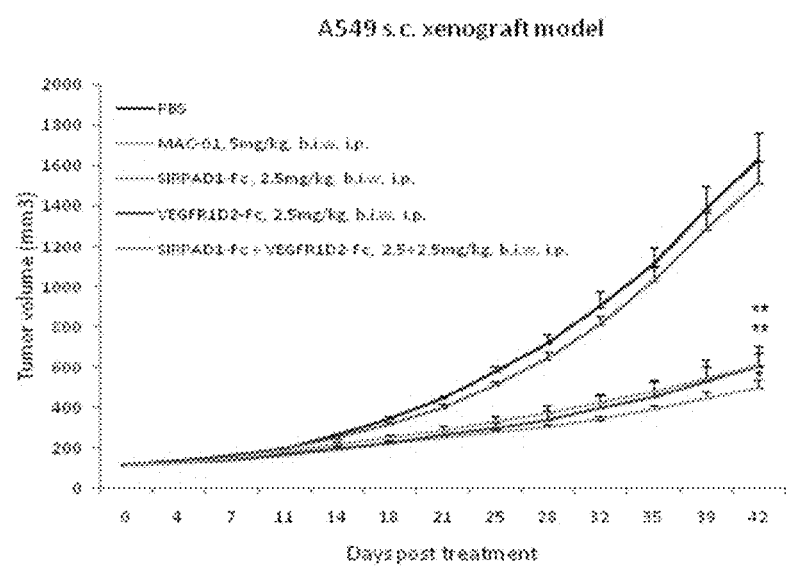
Figure 8: Therapeutic efficacy of SIRPAD1-Fc-VEGFR1D2 (MAC-01) in A549 s.c. xenograft model

RECOMBINANT BI-FUNCTIONAL FUSION PROTEINS, PREPARATIONS AND METHODS FOR TREATING DISEASE

FIELD OF THE INVENTION

The invention relates to a recombinant bi-functional fusion protein, preparation and use thereof, especially its use in tumor therapies.

BACKGROUND OF THE INVENTION

Cancer cells have developed at least three mechanisms to evade a host's immune surveillance: 1) evasion of immune surveillance by T-lymphocytes, by high expression of membrane protein programmed death-ligand 1 and programmed death-ligand 2 (PD-L1 and PD-L2), both of which bind to programmed cell death protein (PD-1) on the surface of T-cell, inducing T-cell apoptosis. 2) evasion of immune surveillance by natural killer (NK) cells. The NKG2D protein on the surface of NK cells, upon binding to the MICA/MICH proteins on the surface of the cancer cells, can activate NK cells which can then kill the cancer cells. However, cancer cells have developed a mechanism that promotes the detachment of MICA/MICB from the cancer cells. The detached MICA/MICH binds to the NKG2D, blocking its activation of the NK cells. 3) Evasion of the immune surveillance of macrophages (Mϕ). Almost all cancer cells express on their surface a high level of Cluster of Differentiation 47 (CD47)[1], which is also known as integrin associated protein (IAP). CD47 binds to the signal regulatory protein α(SIRPα) on the surface of Mϕ, thereby inducing the production of an inhibitory signal, which inhibits the phagocytosis function of Mϕ[2]. Development of effective anti-cancer drugs needs to target these mechanisms [1].

In addition, growth of cancer cells depends on sufficient supply of nutrition. Cancer cells themselves can secrete factors that promote blood vessel growth, such as vascular epithelial growth factors (VEGF). Inhibition of the activity of VEGF will stop blood supply to the tumor, thereby inhibiting the growth of cancer. For example, a drug sold under the tradename AVASTIN™, an FDA approved antibody drug, functions to treat cancers (colon cancer, lung cancer) by inhibiting the biological activities of VEGF. Another protein drug, sold under the trade name ZALTRAP™, which was approved for marketing in August of 2012, for treating colon cancer, also targets VEGF. However, these drugs only inhibit cancer cell growth to certain extent, and cannot eliminate the cancer cells.

Signal Regulatory Protein is a family of trans-membrane proteins, with three members: SIRPα (CD172a), SIRPβ (CD172b), SIRPγ (CD172g). All three members comprise a similar extracellular region, but different intracellular domains. The extracellular domain comprises three Ig-like regions, where the first Ig-like region is an Ig-V region, while the second and third regions are IG-C regions.

The intracellular domain of SIRPα (CD172a) contains two inhibitory signaling regions that can inhibit signal transduction and corresponding cell functions. The intramembrane domains of SIRPβ (CD172b) and SIRPγ (CD172g) are very short, and do not contain a signal transduction region, but SIRPβ (CD172b) may function through an adaptor protein, e.g. DAP12 for signal transduction (see FIG. 1). SIRPs are primarily expressed on macrophages (Mϕ), dendritic cells (DC) and neurons.

CD47 is also a transmembrane glycoprotein belonging to the immunoglobulin superfamily, and is expressed on the surface of all cell types including red blood cells. Ligands for CD47 include integrins, thrombospondin-1 and SIRPs. CD47 has many biological functions, including in cell migration, activation of T-cells and DCs, and neural development. In addition, CD47, by interacting with SIRPα, can inhibit the phagocytosis of macrophages. By emitting a "do not attack" signal, CD47 protects normal cells, such as blood cells, from being attacked by macrophages.

As mentioned above, many tumor or cancer cells overexpress CD47, which, by binding to the SIRPα on the cell surface of macrophages, prevent phagocytosis of the cancer cells by macrophages. Cancer cells that over-express CD47 include acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer. Injection of tumor-bearing mice with CD-47 specific antibody can significantly inhibit tumor growth in vivo[3-4]. Cancer cells in mice carrying human leukemia cells were eliminated completely when the same antibody was injected into the mice[5].

VEGFs are a family of secreted glycoproteins, with a molecular weight of about 40 kDa. This family has 5 members, including VEGF-A, VEGF-B, VEGF-C, VEGF-D, and PIGF. There are three VEGF receptors (VEGFRs), including VEGF VEGFR, and VEGFR3, each of which can bind selectively with different ligands. For example, VEGFR1 binds with VEGF-A, VEGF-B, and PIGF, VEGFR2 binds with VEGF-A, VEGF-C, and VEGF-D, but not PIGF; VEGFR3 binds only with VEGF-C and VEGF-D. The receptors have different functions. VEGFR1 binds to VEGF-A with very high affinity, 10 times higher than VEGFR2, so it functions to negatively regulate VEGFR2. VEGFR2 induces vascular endothelial cell growth, promoting growth of blood vessels. VEGFR3, on the other hand, is related to lymphatic duct development and growth. Of all VEGFs and their receptors, it can be said that VEGF-A and VEGFR2 are the most important, as in certain disease states, (e.g. cancer and age-related macular degeneration), over secretion of VEGF-A, which then binds to VEGFR2, will cause abnormal vascular growth, resulting in disease development or aggravation. Therefore, VEGF-A and VEGFR2 are both important drug targets.

An anti-VEGF monoclonal antibody, sold under the tradename BENAVIZUMAB™, was approved for marketing in 2004, and is indicated for metastatic colon cancer, lung cancer and renal cancer. A recombinant protein drug sold under the tradename ZALTRAP™, also known as VEGF-Trap, which also targets VEGF, was approved for marketing to treat metastatic colon cancer in 2012. Another antibody drug under the tradenaine RAMUCIRUMAB™, targeting VEGFR2, is undergoing a phase III clinical trial. No anti-CD47 drug is on the market, and all are in pre-clinical stage.

There is no report so far of any single molecule drug that targets both CD47 and VEGF, and the present invention satisfies this need.

SUMMARY OF THE INVENTION

The present invention discloses a recombinant bi-functional fusion protein, comprising an Ig region of an extracellular domain of a signal-regulator protein (SIRP), linked via an Fc fragment of an Ig, to an Ig region of an extracellular domain of VEGFR, wherein the protein can bind to CD47 and VEGF simultaneously, blocking the binding of CD47 with the SIRP on the cell surface of macrophages to stimulate the phagocytosis of tumor cells by macrophages, and inhibiting the growth of vascular endothelial cells induced by VEGF. The present application also provides a nucleic acid molecule encoding the recombinant bi-functional fusion protein and an expression vector expressing the protein, a method for producing the protein and a method for treating a disease over-expressing CD47 or VEGF.

In one embodiment, the recombinant bi-functional fusion protein of the present invention comprises an Ig-like region of an extracellular domain of a signal-regulator protein (SIRP), linked via a linker, to an Ig-like region of an extracellular domain of VEGF Receptor (VEGFR), wherein the protein can bind to CD47 and VEGF, blocking the binding of CD47 to the SIRP on the cell surface of macrophages to stimulate the phagocytosis of tumor cells by macrophages, and inhibiting the growth of vascular endothelial cells induced by VEGF.

In one embodiment, the signal-regulatory protein in the recombinant bi-functional fusion protein is SIRPα, and the Ig-like region of the extracellular domain of the signal-regulator protein is SIRPαD1.

In one embodiment, the VEGFR in the recombinant bi-functional fusion protein is VEGFR1, and the Ig-like region of VEGFR1 is a second Ig region of the extracellular domain of VEGFR1 (VEGFR1D2).

In one embodiment, the linker of the recombinant bi-functional fusion protein is an Fc fragment of an Ig. In one embodiment, the Fc fragment is an Fc fragment of IgG1.

In one embodiment, the recombinant bi-functional fusion protein comprises a second Ig region of an extracellular domain of human. VEGFR1 (SIRPαD1-Fc-VEGFR1D2), linked via Fc fragment of human IgG1 to the first Ig region of the extracellular domain of SIRPα(SIRPαD1). In one specific embodiment, the recombinant bi-functional fusion protein of the present invention comprises an amino acid sequence that is 95% identical to that shown in SEQ ID NO: 8. In one embodiment, the amino acid sequence identity between the recombinant bi-functional fusion protein of the present invention and SEQ ID NO: 8 is at least 98%. In one embodiment, the amino acid sequence identity between the recombinant bi-functional fusion protein of the present invention and SEQ ID NO: 8 is at least 99%. In one embodiment, the recombinant bi-functional fusion protein of the present invention comprises an amino acid sequence of SEQ ID NO: 8.

In another embodiment, the present invention provides a polynucleotide molecule encoding the recombinant bi-functional fusion protein of the invention, which comprises an Ig-like region of an extracellular domain of a signal-regulator protein (SIRP), linked via a linker, to an Ig-like region of an extracellular domain of VEGF Receptor (VEGFR), wherein the protein can bind to CD47 and VEGF, blocking the binding of CD47 to the SIRP on the cell surface of macrophages to stimulate the phagocytosis of tumor cells by macrophages, and inhibiting the growth of vascular endothelial cells induced by VEGF.

In one embodiment, the polynucleotide molecule of the present invention encodes a recombinant bi-functional fusion protein which comprises SIRPα, and preferably SIRPαD1. In one embodiment, the polynucleotide molecule of the present invention encodes a recombinant bi-functional fusion protein which comprises VEGFR1, and preferably the second Ig region of the extracellular domain of VEGFR1 (VEGFR1D2).

In one embodiment, the polynucleotide molecule of the present invention encodes a recombinant bi-functional fusion protein which comprises an Fc fragment of an Ig as a linker, preferably, an Fc fragment of IgG1 as a linker.

In one embodiment, the polynucleotide molecule of the present invention encodes a recombinant bi-functional fusion protein which comprises a second Ig region of an extracellular domain of human VEGFR1 (SIRPαD1-Fc-VEGFR1D2), linked via Fc fragment of human IgG1 to the first Ig region of the extracellular domain of SIRPα (SIRPαD1). In one embodiment, the polynucleotide molecule of the present invention encodes a recombinant bi-functional fusion protein which comprises an amino acid sequence that is 95% identical to that shown in SEQ ID NO: 8. In one embodiment, the amino acid sequence identity between the recombinant bi-functional fusion protein of the present invention and SEQ ID NO: 8 is at least 98%. In one embodiment, the amino acid sequence identity between the recombinant bi-functional fusion protein of the present invention and SEQ ID NO: 8 is at least 99%. In one embodiment, the polynucleotide molecule of the present invention encodes a recombinant bi-functional fusion protein which comprises an amino acid sequence of SEQ ID NO: 8.

In another embodiment, the present invention provides an expression vector comprising a polynucleotide of the present invention that encodes a recombinant bi-functional fusion protein.

In another embodiment, the present invention provides host cell comprising an expression vector of the present invention.

In another embodiment, the present invention provides a pharmaceutical composition, comprising recombinant bi-functional fusion protein of the invention, and at least one adjuvant.

In another embodiment, the present invention provides a method for treating a disease caused by over-expression of CD47, or over expression of VEGF, or both, comprising administering to a patient or a subject a therapeutically effective amount of the pharmaceutical composition of the present invention. In another embodiment, the present invention provides the use of the recombinant bi-functional fusion protein in the manufacture of a pharmaceutical composition for the treatment of a disease caused by over-expression of CD47, or over expression of VEGF, or both.

In one embodiment, the method of the present invention is for treating a disease selected from the group consisting of acute myelocytic leukemia (AML), chronic myelocytic leukemia (CML), acute lymphoblastic leukemia (ALL), non-Hodgkin's lymphoma (NHL), multiple myeloma (MM), Bladder cancer, ovarian cancer, prostate cancer, lung cancer, colon cancer, breast cancer, pancreatic cancer, and renal cell carcinoma. In another embodiment, the present invention provides an method for treating Crohn's disease, allergic asthma and rheumatoid arthritis.

In one embodiment, a method for treating a disease caused by enhanced VEGF function and activity according to the present invention is for treating a disease selected from the group consisting of age-related macular degeneration, AMD, diabetic retinopathy, liver fibrosis and angiosarcoma.

DESCRIPTION OF THE DRAWINGS

FIG. 1 is a schematic diagram of the structure of SIRPs.

FIG. 2A and 2B are schematic diagram of the structure and mechanism of action of SIRPαD1-Fc-VEGFR1D2 respectively.

FIGS. 3A and 3B show the nucleic acid (SEQ ID NO: 7) and amino acid sequence (SEQ ID NO: 8) of SIRPαD1-Fc-VEGFR1D2 respectively.

FIG. 4 shows protein electrophoresis analysis of SIRPαD1-Fc-VEGFR1D2.

FIG. 5A and 5B show the results of a target-binding activity analysis.

FIG. 6 shows the results of a target inhibiting assay.

FIG. 7A and 7B show the results of an in vivo anti-tumor assay.

FIG. 8 shows the therapeutic efficacy of MAC-01 in A549 s.c. xenograft model. A group (n=6 for each group) treated with MAC-01 was analyzed and compared to that of SIRPAD1-Fc, VEGFR1D2-Fc, and combination of SIRPAD1-Fc plus VEGFR1D2-Fc. The dosage for each molecule is as follows: MAC-01: 5 mg/kg; SIRPAD1-Fc and VEGFR1D2-Fc: 2.5 mg/kg either as single or combination. Treatment was started when tumor volume reached 100-200 mm$^3$ by i.p. injection, twice a week for 4 weeks.

DETAILED DESCRIPTION OF THE INVENTION

There are principally three different approaches to targeting two or more pharmacologies of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems can reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single compound. The design and validation of such multifunctional compounds are more complex and require substantial investigation into the optimal ratio of target activities in the molecule, but the unified pharmacokinetics may yield matched pharmacodynamic activities at the molecular targets. Multifunctional molecules may also be amenable to fixed dose combination with other drugs thereby combining three or even four pharmacologies in a single pill to produce further increments in efficacy.

Through diligent experimentation, the present inventor has invented a novel recombinant, bi-functional fusion protein, which can attack tumors, via two mechanisms of actions, one to interrupt the blood supply with the tumor tissue, the other to induce tumor cell phagocytosis by macrophages.

In one embodiment, the recombinant bi-functional fusion protein of the present invention comprises an Ig-like region of the extracellular domain of a signal-regulator protein (SIRP), linked via a linker peptide, to an Ig-like region of the extracellular domain of VEGFR. This protein can bind to CD47 and VEGF simultaneously, blocking the binding of CD47 to the SIRP on the cell surface of macrophages, thereby stimulates the phagocytosis of tumor cells by macrophages, and inhibits the growth of vascular endothelial cells induced by VEGF.

The fusion protein of the present invention comprises two target-binding fragments (e.g. SIRPαD1 and VEGFR1D2) and a linker, (e.g. a Fc fragment). A person of ordinary skills in the art will recognize that there are many design choices for selecting any of the above three components.

Linkers serve primarily as a spacer between a polypeptide and a second heterologous polypeptide or other type of fusion polypeptides. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those of skill in the art. In one embodiment, the 1 to 20 amino acids may be selected from glycine, alanine, proline, asparagine, glutamine, and lysine. In one embodiment, a linker is made up of a majority of amino acids that are sterically unhindered, such as glycine and alanine. Exemplary linkers are polyglycines (particularly (Gly)$_5$, (Gly)$_8$, poly(Gly-Ala), and polyalanines. One exemplary suitable linker as shown in the Examples below is (Gly)$_4$Ser (SEQ ID NO: X). In a further embodiment, the bi-functional fusion protein of the present invention can comprise a "hinge linker", that is a linker sequence provided adjacent to a hinge region or a partial hinge region of an IgG. Hinge linker sequences may also be designed to improve manufacturability and stability of the bi-functional fusion protein of the present invention.

Linkers may also be non-peptide linkers. For example, alkyl linkers such as —NH—, —(CH$_2$)s-C(O)—, wherein s=2-20 can be used. These alkyl linkers may further be substituted by any non-sterically hindering group such as lower alkyl (e.g., C$_{1-6}$ lower acyl, halogen (e.g., Cl, Br), CN, NH$_2$, phenyl, etc.

The bi-functional fusion protein of the present invention can also be attached to a non-polypeptide molecule for the purpose of conferring desired properties such as reducing degradation and/or increasing half-life, reducing toxicity, reducing immunogenicity, and/or increasing the biological activity. Exemplary molecules include but are not limited to linear polymers such as polyethylene glycol (PEG), polylysine, a dextran; a lipid; a cholesterol group (such as a steroid); a carbohydrate, or an oligosaccharide molecule.

For example, it is preferable when making design choices regarding orders of linkage, one should minimize the effect of one component on the spatial configuration of the other component, such that they both retain high binding affinity to their respective targets. A linkage order may be SIRPαD1-Fc-VEGFR1D2, or SIRPαD1-VEGFR1D2-Fc, or VEGFR1D2-SIRPαD1-Fc. Also, an ordinarily skilled artisan will recognize that the molecular weight of the recombinant bi-functional fusion protein should be minimized to facilitate production of the fusion protein, so long as the target-binding affinity is not compromised.

For example, the linker protein fragment may be an Fc fragment, or other suitable linker protein. The Fc fragment may be 232 amino acids in size, and comprises a cystine in the hinge region, two cystines in the CH2 region and two cystines in the CH3 region. The cystine in the hinge region contributes to the formation of disulfide bond between two monomers, thereby generating a homodimer, while the cystines in the CH2 and CH3 regions can form intrachain disulfide bonds to stabilize the protein.

Immunoglobulins include IgG, IgA, IgM, IgD and IgA, among which IgG is the most abundant and relatively stable. It is preferred in the present invention as its Fc fragment exhibits the highest binding activity with *staphylococcus* Protein A and therefore can be easily purified.

For example, all of the Ig regions of the extracellular region of SIPR (SIRPα, SIRPγ) capable of binding with CD47 may be used in the fusion protein. The same is true for the Ig-like regions of the extracellular region of VEGFR. The D2 of VEGFR1 has been known to bind to VEGF with the highest activity, thus is preferred in the present invention.

Preferably, human-derived sequence is used in human cancer therapies, as the strong immunogenicity of the proteins or peptides from non-human animals may lead to allergy and other adverse effects. However, other animal proteins or peptides may also be used in the present invention based on different application purposes.

In one embodiment, the signal regulatory protein in the recombinant bi-functional fusion protein of the present invention is SIRPα. The Ig-like region of the extracellular domain of the said signal regulatory protein is SIRPαD1.

In one embodiment, the VEGFR in the recombinant bi-functional fusion protein of the present invention is VEGFR1, and the Ig-like region of the VEGFR1 is the second Ig-like region of the extracellular domain of VEGFR1 (VEGFR1D2).

In one embodiment, the Fc fragment in the recombinant bi-functional fusion protein of the present invention is the Fc fragment of IgG-1.

In one embodiment, the recombinant bi-functional fusion protein of the present invention comprises the first Ig-like region of the extracellular domain of human SIRPα, linked via the Fc fragment of human IgG1 to the second Ig-like region of the extracellular domain of VEGFR1 (VEGFR1D2), generating SIRPαD1-Fc-VEGFR1D2.

In one embodiment, the amino acid sequence of the recombinant bi-functional fusion protein of the present invention is shown in FIG. 3B (SEQ ID NO: 8). In one embodiment, the bi-functional recombinant fusion protein comprises a polypeptide having the sequence set forth in SEQ ID NO: 8. In another embodiment, the polypeptide has an amino acid sequence with at least 80%, 85%, 90%, 95%, 98% or 99% identity to the polypeptides above, wherein the polypeptide is capable of binding to both CD47 and VEGF, and is able to inhibit tumor cell growth.

In another aspect the present invention provides an isolated nucleic acid molecule comprising a polynucleotide encoding a bi-functional recombinant fusion protein comprises a polypeptide having the sequence set forth in SEQ ID NO: 8. In another embodiment, the polypeptide has an amino acid sequence with at least 80%, 85%, 90%, 95%, 98% or 99% identity to the polypeptides above, wherein the polypeptide is capable of binding to both CD47 and VEGF, and is able to inhibit tumor cell growth.

The present invention also discloses a pharmaceutical composition comprising the aforementioned recombinant bi-functional fusion protein, and at least one pharmaceutically acceptable excipient. If needed, one or more pharmaceutically acceptable carriers or excipients may also be included in the pharmaceutical composition. The carriers include diluents, vehicles, bulking agents, bonding agents, wetting agents, disintegrating agents, absorption enhancers, surfactants, sorption carriers, lubricants etc. ordinary in the pharmaceutics.

Such compositions comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly(2-hydroxyethyl-methacrylate) (Langer et al., J. Biomed. Mater. Res., 15:167-277, (1981); Langer et al., Chem. Tech., 1.2:98-105 (1982)), ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the bi-functional fusion protein of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the polypeptide product(s) but prevent the destruction of the cells by the patient's immune system or by other detrimental factors from the surrounding tissues.

A gene therapy in vivo is also envisioned wherein a nucleic acid molecule encoding the bi-functional fusion protein of the present invention, or a derivative thereof is introduced directly into the subject. For example, a nucleic acid sequence encoding a bi-functional fusion protein of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present invention is to provide methods preparing the above recombinant bi-functional fusion protein and the pharmaceutical composition comprising it. In one embodiment, the preparation method comprises the steps of (1) providing an encoding polynucleotide molecule; (2) constructing an expression vector comprising the polynucleotide molecule of (1); (3) transfecting or transforming suitable host cells with the expression vector in (2) and cultivating to express the protein in the host cells; and (4) purifying the protein. The preparation may be carried out with proven and well-known technologies by an ordinarily skilled artisan.

Another object of the present invention is to provide method of treating cancer using the pharmaceutical composition of the present invention comprising administrating an effective amount of the aforementioned pharmaceutical composition to the patients or subjects in need thereof in one embodiment, the pharmaceutical composition is used to treat CD47-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer and renal cancer.

In one embodiment, the pharmaceutical composition can be used to treat other related conditions over-expressing CD47, including but not limited to Crohn's disease, allergic asthma, rheumatoid arthritis.

In one embodiment, the pharmaceutical composition can be used in diseases in which it is desired to inhibit the function or activity of VEGF, including but not limited to age-related macular degeneration (AMD), diabetic retinopathy (DR), liver fibrosis, angiosarcoma, etc.

Also, the present invention provides a polynucleotide molecule encoding the recombinant bi-functional fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACS) and human artificial episomal chromosomes (HAECs).

The present invention provides host cells comprising the above expression vectors. The host cells may be transformed or transfected with the expression vectors. Suitable host cells include prokaryocytes, yeasts and other eukaryotes. Preferably, *Escherichia coli*, yeast or mammalian cell lines (such as COS or CHO) are used.

The recombinant bi-functional fusion protein of the present invention (SIRPαD1-Fc-VEGFR1D2) comprises the first Ig-like region of the extracellular of domain of the human signal-regulatory protein (SIRPαD1 the second region the extracellular domain of the human VEGFR1 (VEGFR1D2) and the Fc fragment of the human IgG1. The protein is a homodimer, with a molecular weight of 100 kDa. A stably-expressing cell line of Chinese hamster ovary (CHO) cells was obtained by screening, and 100 milligrams of the fusion protein was obtained. It is confirmed in vitro that, the protein can bind to CD47 and VEGF simultaneously, block the binding of CD47 with SIRP on the surface of macrophages, promote phagocytosis of the tumor cells by macrophages, and inhibit the growth of vascular endothelial cells induced by VEGF. SIRPαD1-Fc-VEGFR1D2 exhibited potent efficacy on CD47-positive tumor cells HL60 in in-vivo tests, and may eliminate the tumor completely. This is accomplished by inhibiting the angiogenesis in the tumor tissue and stimulating the phagocytosis by macrophages.

The present invention is directed to two crucial cancer targets, SIRPα and VEGF. Although blocking SIRPα may promote the phagocytosis of tumor cells by macrophages (Mφ) but large tumors would not be phagocyted effectively because of ample blood supply. Blocking VEGF alone also fails to eliminate the tumor. When SIRPα and VEGF are blocked simultaneously, the tumor becomes more susceptible to the phagocytosis by macrophages (Mφ) with growth being inhibited, and can be eliminated completely.

The present invention is now further described with the non-limiting examples below.

EXAMPLES

Example 1

SIRPαD1-Fc-VEGFR1D2 Binds to CD47 and VEGF, and Inhibits HL60 Tumor Growth

1. Construction of SIRPαD1-Fc-VEGFR1D2 Expression Vector

Plg-Tail (R&D Systems) was employed. Before cloning, Plg-Tail was engineered, by amplifying the Fc encoding sequence with primers 1 and 2, deleting the stop codon at the carboxyl terminal of Fc, and cloning the PCR product into the EcoRI/XhoI site in plg-Tail. The encoding sequence for SIRPαD1 was amplified with primers 3 and 4 from the THP-1 (ATCC® TIB-202™) cells, and the encoding sequence for VEGFR1D2 was amplified with primers 5 and 6 from the HUVEC (ATCC® PCS-100-010™) cells. The two PCR products were cloned into the HindIII/EcoRI and XhoI/XbaI sites in the engineered plg-Tail vector, respectively, thus generating vector pSIRPαD1-Fc-VEGFR1D2.

TABLE 1

PCR primers

| No. | Primer sequence (5'-3') | target | endo-nuclease |
|---|---|---|---|
| Primer 1: | CGGAATTCGAGCCC AAATCTTGTG (SEQ ID No: 1) | Human IgG1 | EcoRI |
| primer 2: | CATGCTCGAGTTTA CCCGGAGACAGGGA G (SEQ ID No: 2) | Human IgG1 | XhoI |
| primer 3: | CCCAAGCTTGGGGC CACCATGGAGCCCG CCGGCCCGGCCC (SEQ ID No: 3) | SIRPα | HindIII |
| primer 4: | CGGAATTCGTGCTG AGGTGTGGCCCTCG CC (SEQ ID No: 4) | SIRPα | EcoRI |
| primer 5: | CATGCTCGAGAATA GTGATACAGGTAGA CCTTTC (SEQ ID No: 5) | VEGFR1 | XhoI |
| primer 6: | GCATCTAGAGGGTT AGATTGTATTGGTT TGTCGATG (SEQ ID No: 6) | VEGFR1 | XbaI |

Notes:
Gene specific sequences were shown in bold, and endonuclease recognition sites were underlined 2. Protein Expression and Purification The complete cell culture media DMEM (10% FBS) containing CHO cells was added into a 24-well plate in 0.5 ml per well, and the plate was kept in the incubator for 24 hours. For transfection, 0.5 μg plasmid DNA and 2 μl lipofectamine 2000 (Cat#11668-027, Invitrogen) were separately dissolved in 50 μl serum-free culture media, then combined at room temperature for 20 minutes, slowly added into wells, and put back into the incubator for 24 hours. The next day, 100 μl serum was taken and used to test for protein expression by enzyme-linked immunosorbent assay (ELISA).

3. Protein Expression Test

Protein expression test was carried out by ELISA with the following steps: the anti-human IgG goat antibody F(ab')2 fragment (Biosource International Inc) was dissolved in PBS phosphate buffer, then added into a 96-well ELISA plate, 20 ng per well. The ELISA plate was placed in refrigerator at 4° C. overnight. For testing, the plate was blocked with blocking solution (PBS, 0.05% Tween-20, 3% skim milk) for 1 hour, then diluted serum was added and incubated for 1 hour at room temperature. After washing with washing solution (PBS, 0.05% Tween-20) for 5 times, horse radish peroxidase (HRP) labeled anti-human IgG rabbit antibody (Jackson. ImmunoResearch Lab) was added and the plate was incubated at room temperature for 1 hour. After washing 5 times, the substrate for HRP was added, and the stop solution (1N $H_2SO_4$) was used to terminate the chromogenic reaction after 2 minutes. The optical density was measured at 450 nm.

4. Screening the Stably-Expressing Cell Line

Transfected cells were subjected to concentration-increasing antibiotic compression screening (Geneticin, Cat#10131035, Invitrogen). The unstable cells were killed gradually, and survived cells were added into five 96-well plates upon dilution, in 0.5-1 cell per well. The plates were placed in incubator for 10-15 days. The wells containing a single clone were tested by ELISA, then the positive cells was propagated, and habitually cultured with serum-free Ex-CELL CD CHO culture media (Cat#14361C-1000ML, SIGMA). After further screening, the cells representing the highest expression level were selected and frozen for use.

5. Protein Production and Purification

The stably-expressing cell line ($3 \times 10^5$/ml) was inoculated into a 2 L shake flask containing 300 ml serum-free culture media, and the shake flask was placed in a shaking bed for culture. After a cell density of $5 \times 10^6$/ml was reached, we obtained the supernatant. The supernatant was purified with Protein A column. The purified protein was substituted to PBS with dialysis (pH 7.0). Protein electrophoresis analysis was employed to ensure a purity of at least 98%.

6. Target Binding Affinity

The binding affinity of SIRPαD1-Fc-VEGFR1D2 to the targets CD47 and VEGF was tested by using flow cytometry and ELISA method.

SEM-K2 cells and HL60 cells were used in the binding affinity test (the former is acute lymphoblastic leukemia cell and the latter is promyelocytic leukemia cell). After wash with PBS, the cells were suspended in PBS with a concentration of $1 \times 10^6$/ml. hIgG (1 µg/ml) was added into the cell suspension, and the suspension was incubated in a refrigerator at 4° C. for 1 hour. The cells were transferred to a 96-well. U-shaped cell culture plate (Cat#163320, Nunc™) after washed with PBS (100 µl per well). Then, SIRPαD1-Fc-VEGFR1D2 with different concentrations was added and the cells were incubated in a refrigerator at 4° C. for 1 hour. The cells suspended after washed with PBS, and were incubated together with FITC labeled anti-human IgG-Fc antibody (Cat#F9512, Sigma). After 1 hour, the cells were tested by flow cytometry (Guava easyCyte 6HT-2L, Millipore).

The binding affinity to VEGF-A was tested by ELISA, with the following steps:

Diluting VEGF-165 with the coating buffer CBS (Sigma-Aldrich Co., Product code: 1001329288 C3041-100CAP) to 1000 ng/ml; adding the solution of 1000 to an ELISA plate (Cat#442404, Nunc™) (in 100 ng per well); placing the coated plate in a refrigerator at 4° C. overnight; during the testing, washing the coated plate with PBS-T of 0.05% once, and then sealing the coated plate with skimmed milk of 3% for 1 hour; adding the diluted SIRP□D1-Fc-VEGFR1D2 (20, 10, 5, . . . 0.01 nM) to the coated plate (100 µl per well); after incubated at room temperature for 1 hour, discarding the sample and washing the solution with PBS-T of 0.05% for 5 times; adding diluted HRP-Rabbit Anti-Human IgG Fc of 1000 (1:20000) (Cat#:309-036-008, Jackson ImmunoResearch Lab); incubating the solution at mom temperature for 1 hour; washing the plate with a washing solution for 5 times; adding HRP substrate; performing the chromogenic reaction without light for 10-20 minutes and terminating the reaction by using 1N $H_2SO_4$; obtaining the OD450 value on a microplate reader.

7. Target Activity Blocking Assay

In order to test whether SIRPαD1-Fc-VEGFR1D2 can block the phagocytosis inhibitory activity induced by the binding of CD47-SIRPα, mixing FITCCFSE labeled SEM-K2 cells and RAW264.7 cells at a RAW264.7:SEM-K2 ratio of 2:1; then culturing the mixture with SIRPαD1-Fc-VEGFR1D2, SIRPαD1-Fc and human IgG-Fc having different concentrations in 6 new cell culture plates; after 4 hours, shaking the plates carefully and sucking the suspended SEM-K2 cells, washing the plates with PBS twice to remove all suspended cells; digesting RAW264.7 cells on the plate wall with Trypsin-EDTA and washing the plates with PBS twice; quantitatively analyzing the phagocytosis ratio of SEM-K2 cells by RAW264.7 cells via flow cytometry.

8. Antitumor Assay

The in vivo antitumor activity of SIRPαD1-Fc-VEGFR1D2 was studied in a HL-60 subcutaneous tumor model. The HL-60 cell line is a well characterized in vitro human leukemia model, derived from a single patient with acute promyelocytic leukemia[6], and has been widely used in xenograft mouse models for therapeutic efficacy of a drug[7-9]. Twenty (20) Balb/c nude mice were injected subcutaneously with leukemia (HL60) cells ($4 \times 10^6$ cells per mouse). When the tumors grew up to 100-150 mm³, the mice were divided into 4 groups: the first group was intraperitoneally injected with PBS; the second group was intraperitoneally injected with VEGFR1D2-Fc; the third group was intraperitoneally injected with SIRPαD1-Fc; the fourth group was intraperitoneally injected with SIRPαD1-Fc-VEGFR1D2. The dosage for each group was 3 mg/kg, and was administered twice a week for 6 times continuously. The volume and weight of the tumors were measured twice a week.

Experimental Results

1. Construction of Expression Vector of SIRPα1-Fc-VEGFR1D2

SIRPαD1-Fc-VEGFR1D2 is a recombinant Fc-fusion protein consisting of the first extracellular domain (D1) of SIRPα and the second extracellular domain (D2) of VEGFR1 linked in between with the Fc fragment of human IgG1, and is named MAC-01. It has the structure as shown in FIG. 2A. SIRPαD1 and VEGFR1D2 are respectively connected to N-terminal and C-terminal by molecular cloning. The sequence of SIRPαD1-Fc-VEGFR1D2 contains 1503 nucleotides (FIG. 3A) wherein the signal peptide coding sequence has 63 nucleotides (in red), SIRPαD1 has 426 nucleotides (in blue), IgG1-Fc has 696 nucleotides (in black), VEGFR1D2 has 306 nucleotides (in green), EcoRI sequence has 6 nucleotides, and XhoI sequence has 6 nucleotides. FIG. 3B shows the corresponding amino acid sequences.

2. Protein Expression Analysis

By using protein electrophoresis (SDS-PAGE), we found that protein molecular weight was larger than 170 kDa (FIG. 4) under non-reducing conditions quite different from the theoretical value (100 kDa). This might be due to protein glycosylation.

3. Target Binding Affinity of SIRPαD1-Fc-VEGFR1D2

By using flow cytometry and ELISA, we analyzed the binding affinity of SIRPαD1-Fc-VEGFR1D2 to VEGF-A. The results showed that SIRPαD1-Fc-VEGFR1D2 bowed both CD47 (FIG. 5A) and VEGF-A (FIG. 5B), respectively having EC50 of 0.1-1.0 nM (CD47) and 0.08-0.15nM (VEGF-A).

4. SIRPαD1-Fc-VEGFR1D2 Promotes Phagocytosis of the Tumor Cells by Macrophages

By using labeled acute lymphoblastic leukemia cell. SEM-K2 and macrophages of mice (RAW264.7), we analyzed the effects of SIRPαD1-Fc-VEGFR1D2 on phagocytosis of the tumor cells. The results showed (FIG. 6) that SIRPαD1-Fc-VEGFR1D2 significantly strengthened the phagocytosis of the tumor cells by macrophages. The effect was dose dependent.

5. Antitumor Activity of SIRPαD1-Fc-VEGFR1D2 Protein

By using the HL60 subcutaneous tumor model, we studied in vivo antitumor activity of SIRPαD1-Fc-VEGFR1D2 protein. As shown in FIG. 7, VEGFR1D2-Fc treatment group showed very limited inhibitory effects on tumor growth and SIRPαD1-Fc treatment group showed obvious inhibitory effects on tumor growth but not sufficient to eliminate the tumor. In contrast, while after the treatment with SIRPαD1-Fc-VEGFR1D2, the mice showed that the tumor size was reduced from 100 mm$^3$ at the beginning of treatment and the tumor almost disappeared at the conclusion of treatment. In the negative control group, the tumor volume of the mice gradually grew over time and reached 1000 mm$^3$ in the end. The experimental results showed that only inhibiting the activity of VEGF has no significant treatment effects on the HL60 tumor, indicating that the growth of HL60 tumor does not largely depend on VEGF. Blocking the inhibition, induced by the tumor, of phagocytosis by macrophages strengthened the phagocytosis of the tumor cells by macrophages, thereby significantly inhibiting the growth of tumor cells. However, if the functions of both VEGF and CD47-SIRP are inhibited, the tumor will be completely eliminated.

The above data indicates that the recombinant bi-functional fusion protein SIRPαD1-Fc-VEGFR1D2 is a new recombinant protein with good dual-target binding affinity. In vivo experimentation shows that SIRPαD1-Fc-VEGFR1D2 protein has significant antitumor activity. In the HL60 model, the tumor can be completely eliminated. The protein principally has two mechanisms to eliminate the tumor: inhibition of blood vessel growth in the tumor, thereby stopping the supply of nutrition needed for tumor growth; binding of CD47 on tumor cell surface to SIRPα on phagocyte surface, thereby destroying self-protection mechanism induced by the tumor, so as to induce strong phagocytosis of the tumor cells by macrophages. These two mechanisms are synergistic, i.e. the tumor volume is reduced due to lack of nutrition and thus the tumor is more easily phagocytosed by macrophages, resulting in elimination of the tumor.

Example 2

MAC-01 Inhibits Lung Cancer (A549) Growth

The above recombinant Fc-fusion protein SIRPAD1-Fc-VEGFR1D2 (MAC-01) was tested on an A549 Lung Cancer Xenograft model. The A549 cell line was first developed in 1972 by D. J. Giard, et al. through the removal and culturing of cancerous lung tissue in the explanted tumor of q 58-year-old caucasian male[10][11]. The A549 xenograft mouse model has been extensively used for efficacy evaluation of many drug candidates[12-15]. Experimental data indicated that MAC-01 can simultaneously bind with both VEGF and CD47 and thus can block respective molecule-mediated signals. When investigated in in vivo lung cancer xenograft model, MAC-01 exhibits a strong anti-tumor activity that is clearly better than that of combination of the single molecules.

Balb/c nude Mice were injected subcutaneously with 5×10$^6$ A549 cells in 200 μL of serum-free medium/matrigel (50:50 v/v). When the average tumor volume reaches 100-200 mm$^3$, 30 mice bearing tumors of suitable size were randomized into 5 groups (6 mice per group) according to tumor volume. Mice were treated through i.p., twice a week for 4 weeks, with either Sing/kg of MAC-01, or 2.5 mg/kg of SIRPAD1-Fc, or 2.5 mg/kg of VEGFR1D2-Fc, or combination of 2.5 mg/kg of SIRPAD1-Fc with 2.5 mg/kg of VEGFR1D2-Fc. PBS treatment was used as negative control. Antitumor effects are expressed as % T/C (treated versus control), dividing the tumor volumes from treatment groups with the control groups and multiplied by 100.

As showed in FIG. 8, treatment with SIRPAD1-Fc alone resulted in minimal tumor growth inhibition with the tumor growth inhibition rate of only 93% T/C. While treatment with VEGFR1D2-Fc lead to dramatic tumor growth inhibition (32% T/C), addition of SIRPAD1-Fc to VEGFR1D2-Fc treatment didn't further enhance VEGFR1D2-Fc-mediated tumor growth inhibition (33% T/C). Promisingly however, treatment with the recombinant bi-functional protein MAC-01 resulted in dramatic tumor growth inhibition (25% T/C) which is significantly more pronounced when compared to that in group treated either with VEGFR1D2-Fc alone, or with the combination of the single molecules (P=0.05). Results of statistic analysis are showed in Table 2.

TABLE 2

Tumor growth inhibition in A549 s.c. xenograft model

| Drugs | Growth inhibition Rate (% T/C) | P value vs PBS | P value vs MAC-01 |
|---|---|---|---|
| MAC-01, 5 mg/kg | 25 | 0.001 | |
| SIRPAD1-Fc, 2.5 mg/kg | 93 | 0.47 | |
| VEGFR1D2-Fc, 2.5 mg/kg | 32 | 0.001 | 0.05 |
| SIRPAD1-Fc + VEGFR1D2-Fc | 33 | 0.001 | 0.05 |

The above results showed that recombinant bi-functional protein MAC-01 has dramatic in vivo anti-tumor activity, most likely through blocking VEGF and SIRP simultaneously.

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

REFERENCES

1. Chao M P, Weissman I L, and Majeti R. The CD47-SIRPα, Pathway in Cancer immune Evasion and Potential Therapeutic Implications. Curr Opin Immunol. 2012, 24: 225-232.
2. Chao M P, Tang C, Pachynski R K, Chin R, Majeti R, Weissman I L. Extranodal dissemination of non-hodgkin lymphoma requires cd47 and is inhibited by anti-cd47 antibody therapy. Blood. 2011, 118:4890-4901.
3. Chao M P, Alizadeh A A, Tang C, Myklebust J H, Varghese B, Gill S, Jan M, Cha A C, Chan C K, Tan B T, Park C Y, et al. Anti-cd47 antibody synergizes with rituximab to promote phagocytosis and eradicate non-hodgkin lymphoma. Cell. 2010, 142:699-713.
4. Majeti R, Chao M P, Alizadeh A A, Pang W W, Jaiswal S, Gibbs K D, Jr, van Rooijen N, Weissman I L. CD47 is an adverse prognostic factor and therapeutic antibody target on human acute myeloid leukemia stem cells. Cell. 2009, 138:286-299.
5. Chao M P, Alizadeh A A, Tang C. Jan M, Weissman-Tsukarnoto R, Zhao F, Park C Y, Weissman I L, Majeti R. Therapeutic antibody targeting of cd47 eliminates human acute lymphoblastic leukemia. Cancer Res. 2011, 71:1374-1384.

6. Collins S J. The HL60 promyelocytic leukemia cell line: proliferation, differentiation, and cellular oncogene expression. Blood. 1987, 70:1233-1244.
7. Xu Y and Scheinberg D A. Elimination of human leukemia by monoclonal antibodies in an athymic nude mouse leukemia model. Clin Cancer Res. 1995, 1:1179-1187.
8. Lin J J, Hsu H Y, et al. Molecular evidence of anti-leukemia activity of gypenosides on human myeloid leukemia HL-60 cells in vitro and in vivo using a HL-60 cells murine xenograft model. Phytomedicine. 2011, 18:1075-1085
9. Sun Y, Xu H J., et al. Crocin Exhibits Antitumor Effects on Human Leukemia HL-60 Cells In Vitro and In Vivo. Evidence-Based Complementary and Alternative Medicine. 2013, 2013:1-7.
10. Thomas L H, Friedland J S, Sharland M, Becker S. Respiratory Syncytial Virus-Induced RANTES Production from Human Bronchial Epithelial Cells Is Dependent on Nuclear Factor-κB Nuclear Binding and Is Inhibited by Adenovirus-Mediated Expression of Inhibitor of κBα. Journal of Immunology. 1998, 161:1007-16.
11. Lin Y, Zhang M, Barnes P F. Chemokine production by a human alveolar epithelial cell line in response to Mycobacterium tuberculosis. Infection and Immunity. 1998, 66:1121-6.
12. Xu X and Prestwich G D. Inhibition of Tumor Growth and Angiogenesis by a Lysophosphatidic Acid Antagonist in a Engineered Three-dimensional Lung Cancer Xenograft Model. Cancer. 2010, 116:1739-1750.
13. Coxon A, Ziegler B, et al. Antitumor activity of motesanib alone and in combination with cisplatin or docetaxel in multiple human non-small-cell lung cancer xenograft models. Mol Cancer. 2012, 11:70.
14. Naumov G N, Nilsson M B, et al. Combined Vascular Endothelial Growth Factor Receptor and Epidermal Growth Factor Receptor (EGFR) Blockade inhibits Tumor Growth in Xenograft Models of EGFR Inhibitor Resistance. Clin Cancer Res. 2009, 15:3484-3494.
15. Magda D, Lecane P, et al. mtDNA depletion confers specific gene expression profiles in human cells grown in culture and in xenograft. BMC Genomics. 2008, 9:521.

What is claimed is:

1. A recombinant bi-functional fusion protein, comprising an Ig-like region of an extracellular domain of a signal-regulatory protein alpha (SIRPα), linked via a linker, to an Ig-like region of an extracellular domain of vascular endothelial growth factor (VEGF) Receptor (VEGFR), wherein the protein can bind to Cluster of Differentiation 47 (CD47) and YEW blocking the binding of CD47 to the SIRP on the cell surface of macrophages to stimulate the phagocytosis of tumor cells by macrophages, and inhibiting the growth of vascular endothelial cells induced by VEGF.

2. The recombinant bi-functional fusion protein according to claim 1, wherein the Ig-like region of the extracellular domain of the signal-regulatory protein is SIRPαD1.

3. The recombinant bi-functional fusion protein according to claim 1, wherein the VEGFR is VEGFR1.

4. The recombinant bi-functional fusion protein according to claim 1, wherein the Ig-like region of VEGFR1 is a second Ig-like region of the extracellular domain of VEGFR1 (VEGFR1D2).

5. The recombinant bi-functional fusion protein according to claim 1, wherein the linker is an Fc fragment of an Ig.

6. The recombinant bi-functional fusion protein according to claim 1, wherein the Fc fragment is an Fc fragment of IgG1.

7. The recombinant bi-functional fusion protein according to claim 1, comprising a second Ig-like region of an extracellular domain of human VEGFR1, linked via Fc fragment of human IgG1 to the first Ig-like region of the extracellular domain of SIRPα (SIRPαD1).

8. The recombinant bi-functional fusion protein according to claim 1, comprising an amino acid sequence which is at least 95% identical to SEQ ID NO: 8.

9. The recombinant bi-functional fusion protein according to claim 8, comprising the amino acid sequence of SEQ ID NO: 8.

10. The recombinant bi-functional fusion protein according to claim 8, comprising an amino acid sequence which is at least 98% identical to SEQ ID NO: 8.

11. The recombinant bi-functional fusion protein according to claim 10, comprising an amino acid sequence which is at least 99% identical to SEQ ID NO: 8.

12. A polynucleotide encoding the recombinant bi-functional fusion protein according to claim 8.

13. A polynucleotide encoding the recombinant bi-functional fusion protein according to claim 9.

14. An expression vector comprising a polynucleotide of claim 12.

15. An expression vector comprising a polynucleotide of claim 13.

16. An isolated host cell comprising the expression vector of claim 14.

17. The isolated host cell of claim 16, wherein the host cell is a prokaryotic cell.

18. The isolated host cell of claim 16, wherein the host cell is a yeast cell.

19. The isolated host cell of claim 16, wherein the host cell is a yeast cell.

20. The isolated host cell of claim 16, wherein the host cell is a mammalian cell.

21. The isolated host cell of claim 20, wherein the host cell is CHO cell.

22. The isolated host cell of claim 20, wherein the host cell is a human cell.

23. A pharmaceutical composition, comprising recombinant bi-functional fusion protein of claim 1, and at least one pharmaceutical adjuvant.

24. A method for treating a disease caused by overexpression of CD47, comprising administering to a patient or a subject a therapeutically effective amount of the pharmaceutical composition according to claim 23.

25. The method according to claim 24, wherein the disease is selected from the group of acute myeloid leukemia (AML), chronic myelocytic leukemia (CML), acute lymphoblastic leukemia (ALL), non-Hodgkin's lymphoma (NHL), multiple myeloma (MM), Bladder cancer, ovarian cancer, prostate cancer, lung cancer, colon cancer, breast cancer, pancreatic cancer, and renal cell carcinoma.

26. The method according to claim 24, wherein the disease is selected from the group of Crohn's disease, allergic asthma and rheumatoid arthritis.

27. A method for treating a disease caused by enhanced VEGF function and activity, comprising administering to a patient or a subject a therapeutically effective amount of the pharmaceutical composition according to claim 23.

28. The method according to claim 24, wherein the disease is selected from age-related macular degeneration, AMD, diabetic retinopathy, liver fibrosis and angiosarcoma.

* * * * *

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Primer 1

<400> SEQUENCE: 1
cggaattcga gcccaaatct tgtg                                              24

<210> SEQ ID NO 2
<211> LENGTH: 29
<212> TYPE: DNA
<213> ORGANISM: Artificial Sequence
<220> FEATURE:
<223> OTHER INFORMATION: Primer 2

<400> SEQUENCE: 2
catgctcgag tttacccgga gacagggag                                         29

<210> SEQ ID NO 3
<211> LENGTH: 40
<212> TYPE: DNA
<213> ORGANISM: Artificial Sequence
<220> FEATURE:
<223> OTHER INFORMATION: Primer 3

<400> SEQUENCE: 3
cccaagcttg gggccaccat ggagcccgcc ggcccggccc                             40

<210> SEQ ID NO 4
<211> LENGTH: 30
<212> TYPE: DNA
<213> ORGANISM: Artificial Sequence
<220> FEATURE:
<223> OTHER INFORMATION: Primer 4

<400> SEQUENCE: 4
cggaattcgt gctgaggtgt ggccctcgcc                                        30

<210> SEQ ID NO 5
```

```
<211> LENGTH: 34
<212> TYPE: DNA
<213> ORGANISM: Artificial Sequence
<220> FEATURE:
<223> OTHER INFORMATION: Primer 5

<400> SEQUENCE: 5
catgctcgag aatagtgata caggtagacc tttc                              34

<210> SEQ ID NO 6
<211> LENGTH: 36
<212> TYPE: DNA
<213> ORGANISM: Artificial Sequence
<220> FEATURE:
<223> OTHER INFORMATION: Primer 6

<400> SEQUENCE: 6
gcatctagag ggttagattg tattggtttg tcgatg                            36

<210> SEQ ID NO 7
<211> LENGTH: 1506
<212> TYPE: DNA
<213> ORGANISM: Artificial Sequence
<220> FEATURE:
<223> OTHER INFORMATION: SIRPaD1-Fc-VEGFR1D2

<400> SEQUENCE: 7
atggagcccg ccggcccggc ccccggccgc ctcggccgc tgctctgcct gctgctcgcc    60
gcgtcctgcg cctggtcagg agtggcgggt gaggaggagc tgcaggtgat tcagcctgac   120
aagtccgtat cagttgcagc tggagagtcg gccattctgc actgcactgt gacctccctg   180
atccctgtgg ggcccatcca gtggttcaga ggagctggac cagcccggga attaatctac   240
aatcaaaaag aaggccactt ccccggggta caactgtttt cagagtccac aaagagagaa   300
aacatggact tttccatcag catcagtaac atcaccccag cagatgccgg cacctactac   360
tgtgtgaagt tccggaaagg gagccctgac acggagttta gtctggagc aggcactgag   420 ctgtctgtgc gtgccaaacc ctctgccccc gtggtatcgg gccctgcggc gagggccaca   480
cctcagcacg aattcgagcc caaatcttgt gacaaaactc acacatgccc accgtgccca   540
gcacctgaac tcctgggggg accgtcagtc ttcctcttcc cccaaaaacc caaggacacc   600
ctcatgatct cccggacccc tgaggtcaca tgcgtggtgg tggacgtgag ccacgaagac   660
cctgaggtca agttcaactg gtacgtggac ggcgtggagg tgcataatgc caagacaaag   720
ccgcgggagg agcagtacaa cagcacgtac cgtgtggtca gcgtcctcac cgtcctgcac   780
caggactggc tgaatggcaa ggagtacaag tgcaaggtct ccaacaaagc cctcccagcc   840
cccatcgaga aaaccatctc caaagccaaa gggcagcccc gagaaccaca ggtgtacacc   900
ctgcccccat cccgggatga gctgaccaag aaccaggtca gcctgacctg cctggtcaaa   960
ggcttctatc ccagcgacat cgccgtggag tgggagagca atgggcagcc ggagaacaac  1020
tacaagacca cgcctcccgt gctggactcc gacggctcct tcttcctcta cagcaagctc  1080
accgtggaca agagcaggtg gcagcagggg aacgtcttct catgctccgt gatgcatgag  1140
gctctgcaca accactacac gcagaagagc ctctccctgt ctccgggtaa actcgagatt  1200
agtgatacag gtagaccttt cgtagagatg tacagtgaaa tccccgaaat tatacacatg  1260
actgaaggaa gggagctcgt cattccctgc cgggttacgt cacctaacat cactgttact  1320
ttaaaaaagt ttccacttga cactttgatc cctgatggaa aacgcataat ctgggacagt  1380
agaaagggct tcatcatatc aaatgcaacg tacaaagaaa tagggcttct gacctgtgaa  1440
```

```
gcaacagtca atgggcattt gtataagaca aactatctca cacatcgaca aaccaataca    1500
atctaa                                                               1506
```

<210> SEQ ID NO 8
<211> LENGTH: 501
<212> TYPE: PRT
<213> ORGANISM: Artificial Sequence
<220> FEATURE:
<223> OTHER INFORMATION: SIRPaD1-Fc-VEGFR1D2

<400> SEQUENCE: 8

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
        50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Val Ser Glu Ser
                85                  90                  95

Thr Lys Arg Glu Asn Met Asp Phe Ser Ile Ser Ile Ser Asn Ile Thr
                100                 105                 110

Pro Ala Asp Ala Gly Thr Tyr Tyr Cys Val Lys Phe Arg Lys Gly Ser
            115                 120                 125

Pro Asp Thr Glu Phe Lys Ser Gly Ala Gly Thr Glu Leu Ser Val Arg
        130                 135                 140

Ala Lys Pro Ser Ala Pro Val Val Ser Gly Pro Ala Ala Arg Ala Thr
145                 150                 155                 160

Pro Gln His Glu Phe Glu Pro Lys Ser Cys Asp Lys Thr His Thr Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Asp Glu Leu Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
```

-continued

```
                    340                 345                 350
Ser Phe Phe Leu Tyr Ser Lys Leu Thr Val Asp Lys Ser Arg Trp Gln
            355                 360                 365

Gln Gly Asn Val Phe Ser Cys Ser Val Met His Glu Ala Leu His Asn
            370                 375                 380

His Tyr Thr Gln Lys Ser Leu Ser Leu Ser Pro Gly Lys Leu Glu Ile
385                 390                 395                 400

Ser Asp Thr Gly Arg Pro Phe Val Glu Met Tyr Ser Glu Ile Pro Glu
                    405                 410                 415

Ile Ile His Met Thr Glu Gly Arg Glu Leu Val Ile Pro Cys Arg Val
                420                 425                 430

Thr Ser Pro Asn Ile Thr Val Thr Leu Lys Lys Phe Pro Leu Asp Thr
            435                 440                 445

Leu Ile Pro Asp Gly Lys Arg Ile Ile Trp Asp Ser Arg Lys Gly Phe
        450                 455                 460

Ile Ile Ser Asn Ala Thr Tyr Lys Glu Ile Gly Leu Leu Thr Cys Glu
465                 470                 475                 480

Ala Thr Val Asn Gly His Leu Tyr Lys Thr Asn Tyr Leu Thr His Arg
                485                 490                 495

Gln Thr Asn Thr Ile
            500
```